United States Patent [19]

Fetizon et al.

[11] 4,306,099

[45] Dec. 15, 1981

[54] METHOD OF PREPARATION OF PERILLIC ALCOHOL AND DERIVATIVES THEREOF

[75] Inventors: Marcel Fetizon, Gif sur Yvette; Jules E. Ecoto, Palaiseau; Sylvain Lazare, Saint Remy les Chevreuse, all of France

[73] Assignee: Synarome H, Fraysse et Cie, Chartres, France

[21] Appl. No.: 158,151

[22] Filed: Jun. 10, 1980

[30] Foreign Application Priority Data

Jun. 19, 1979 [FR] France .................................. 79 15676

[51] Int. Cl.$^3$ ...................... C07C 29/00; C07C 35/14; C07C 35/18
[52] U.S. Cl. ............................... 568/823; 252/174.11; 252/522 R; 424/358; 560/249; 568/829; 568/446
[58] Field of Search ......................... 568/823, 827, 826

[56] References Cited

U.S. PATENT DOCUMENTS 2,898,380 8/1959 Herrlinger et al. .................. 568/827
3,281,479 10/1966 Arakawa et al. .................... 568/827
3,957,856 5/1976 Ansari et al. ........................ 568/826

FOREIGN PATENT DOCUMENTS 2162882 7/1972 Fed. Rep. of Germany .
1183849 2/1959 France .
1094875 12/1967 United Kingdom .

OTHER PUBLICATIONS

Kergomard, Bulletin de la Societe Chimique de France, vol., 7, Jul. 1958, pp. 1174–1178.
Chemical Abstracts, vol. 69, 10547X, (1968).

*Primary Examiner*—Natalie Trousof
*Assistant Examiner*—Vera C. Clarke
*Attorney, Agent, or Firm*—Young & Thompson

[57] ABSTRACT

Perillic alcohol is prepared by allowing beta-pinene epoxide to react with an aqueous suspension of mercuric salt, after this, the organic fraction is removed from the reaction medium, and treated with an inorganic acid. If the inorganic fraction is left untreated, 7, 8-dihydroxy-1-paramenthene is obtained. Perillic alcohol and derivatives thereof are used in the fields of perfumery, cosmetics and soaps.

10 Claims, No Drawings

METHOD OF PREPARATION OF PERILLIC ALCOHOL AND DERIVATIVES THEREOF

This invention concerns a method of preparation of perillic alcohol or 7-hydroxy-1,8-paramenthadiene and of 7,8-hydroxy-1-paramenthene, which is a derivative of perillic alcohol.

Perillic alcohol, which has the following formula:

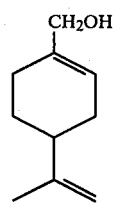

is remarkable for its pleasant odour. This compound is widely used as a perfume in cosmetic, perfumery and soaps.

Various methods are known for the preparation of perillic alcohol.

A first method involes the oxidation of alpha- or beta-pinene by a tetracarboxylate of lead (see British Patent Number 1094875).

A second method known involves the oxidation of alpha- or beta-pinene (obtained from pines) with benzoyl peroxide in the presence of copper salts (see the German Patent Application Number 2162882).

Both methods have the drawbacks of poor yields, and the subsequent production of a mixture of compounds from which it is difficult to extract pure perillic alcohol.

In another recognised method, the starting material is limonene. This procedure is costly, since limonene itself is an expensive product.

The aim of the present invention is to provide a method for the preparation of perillic alcohol having, amongst other advantages, that of economy, of easy performance and of excellent yields.

According to the invention, the method is as follows: beta-pinene epoxide is allowed to react with an aqueous suspension of mercuric salt, the organic fraction so obtained is removed from the reaction medium, and treated with an inorganic acid.

The reaction is rapid (about ten minutes), and does not require heat.

The reaction is as follows:

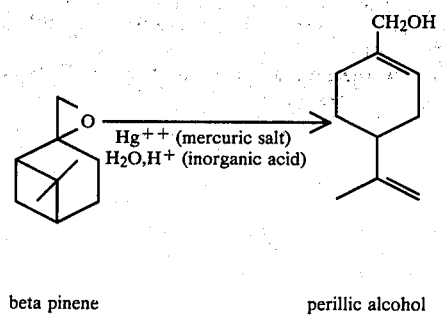

beta pinene    perillic alcohol

The mercuric salt used is preferably mercuric sulphate ($HgSO_4$) or else mercuric chlorate ($Hg(ClO_4)_2$).

In order to obtain a yield approaching that of 100%, it is preferable to use a quantity of mercuric salt in excess of the stoichiometric equivalent theoretically necessary.

The reaction is also favoured if it takes place in the presence of a water-miscible organic solvent, such as tetrahydrofuran. The reaction medium thus formed is perfectly homogeneous.

The following example is a non-limiting operational method for the preparation of perillic alcohol.

EXAMPLE I

Take 2.96 gm. of $HgSO_4$ suspended in 10 cc. of $H_2O$ and 10 cc. of tetrahydrofuran, add to it 1.5 gm. of beta-pinene epoxide. Allow to react until completion in ten minutes. Check that the reaction is complete by thin-layer chromatography. The organic fraction is removed by ether, and washed with dilute sulphuric acid (or with any other dilute inorganic acid) and then with an aqueous solution of $Na_2CO_3$, anhydrous, the solvent is removed and distilled. It is separated by high-pressure liquid chromatography to give a sample for analysis.

The mercuric sulphate is recovered by evaporation of the aqueous fraction.

Perillic alcohol is thus obtained with a yield of over 98%.

Beta-pinene epoxide, the starting material for this reaction, is easily obtained by selective oxidation of beta-pinene.

The epoxide of beta-pinene used may be levo-, dextro-, or racemic.

Experience has shown the surprising result that by a slight modification of the operational method of the procedure used in the invention, it is possible to obtain a perfectly stable derivative of perillic alcohol, 7,8-dihydroxy-1-paramenthene, which has the following formula:

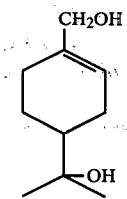

The preparation of 7,8-dihydroxy-1-paramenthene involves the same method as that for the preparation of perillic alcohol, but without the addition of inorganic fraction.

7,8-dihydroxy-1-paramenthene has a very pleasant "fresh, slightly green, aromatic" smell, which makes it suitable for use in the odorizing mixtures used in perfumery, cosmetic products, soaps and detergents, in air-fresheners and in industrial products.

An example of the method of preparation of 7,8-dihydroxy-1-paramenthene is given below:

EXAMPLE II

By the same method as that used in Example I, but using 6 gm. $Hg(ClO_4)_2$ and 2 gm β-pinene epoxide (or 2.96 gm $HgSO_4$ and 1.5 gm. β-pinene epoxide) and omitting the final washing with inorganic acid, 7,8-dihydroxy-1-paramenthene is obtained in a virtually pure state, and a yield of between 98% annd 100%. It can be used without further treatment.

High pressure chromatography is used to obtain a sample for analysis.

Analysis reveals a molecular composition of $C_{10}H_{18}O_2$.

The structure of the compound is determined by nuclear magnetic resonance (NMR), using $C_{13}$ and $H_1$.

7,8-dihydroxy-1-paramenthene monoacetate, which has the following formula:

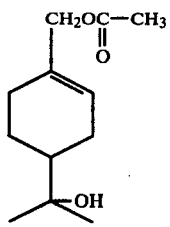

is prepared by classical esterification, using acetic acid.

This compound is also characterised by a very pleasant smell of woods, incense, balsalm.

The higher esters such as the monopropionate, the monobutylate etc. can also be prepared by conventional esterification.

The aldehyde, which has the following formula:

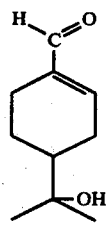

can also be prepared by the usual method for the dehydration of primary alcohols.

The following list is non-exhaustive, giving examples of compounds including a derivative of the invention:

| Example I: | |
|---|---|
| Linalyl acetate | 17 (parts by weight) |
| terpenyl acetate | 15 (parts by weight) |
| Geranyl acetate | 5 (parts by weight) |
| Coumarin | 7 (parts by weight) |
| Romarin | 10 (parts by weight) |
| Terpineol | 7 (parts by weight) |
| Nopol | 20 (parts by weight) |
| Ethyl amylacetone | 2 (parts by weight) |
| 7,8-dihydroxy-1-paramenthene | 17 (parts by weight) |
| Example II: | |
| Hexyl cinnamic aldehyde | 10 (parts by weight) |
| Geraniol | 10 (parts by weight) |
| Dimethyl benzyl carbinol | 10 (parts by weight) |
| Terpenyl acetate | 15 (parts by weight) |
| Synthesised jasmine | 30 (parts by weight) |
| Synthesised orange blossom | 2 (parts by weight) |
| Heliotropine | 1 (parts by weight) |
| Styrax essence | 2 (parts by weight) |
| Linalol | 5 (parts by weight) |
| Citral dimethyl acetal | 3 (parts by weight) |
| Synthesised rose | 6 (parts by weight) |
| 7,8-dihydroxy-1-paramenthene | 6 (parts by weight) |
| Example III: | |
| Coumarin | 10 (parts by weight) |
| Non-allergic bergamot | 10 (parts by weight) |
| Phenyl ethylic alcohol | 4 (parts by weight) |
| Methylionone | 15 (parts by weight) |
| Vetiver | 10 (parts by weight) |
| Cedryl acetate | 7 (parts by weight) |
| vetiveryl acetate | 5 (parts by weight) |
| Synthesised jasmine | 6 (parts by weight) |
| Sandalwood | 10 (parts by weight) |
| Aldehyde C.11 1/10 | 3 (parts by weight) |
| Aldehyde C.12 1/10 | 1 (parts by weight) |
| Geraniol | 5 (parts by weight) |
| Citronellol | 3 (parts by weight) |
| 7,8-dihydroxy-8-parammenthene acetate | 11 (parts by weight) |

What is claimed is:

1. A method for the preparation of perillic alcohol comprising the reaction of beta-pinene epoxide with an aqueous suspension of mercuric salt, the extraction of the organic fraction of the reaction medium and the treatment of said organic fraction with an inorganic acid.

2. A method according to claim 1, wherein said mercuric salt is selected from the group consisting of mercuric sulphate and mercuric chlorate.

3. A method according to claim 1, wherein said reaction is performed with a stoichiometric excess of the mercuric salt.

4. A method according to claim 1, wherein said reaction is performed in the presence of a water-miscible organic solvent.

5. A method according to claim 4, wherein said solvent is tetrahydrofuran.

6. A method for the preparation of 7,8-dihydroxy 1-paramenthene comprising the reaction of beta-pinene epoxide with an aqueous suspension of mercuric salt and the extraction of the organic fraction from the reaction medium.

7. A method according to claim 6, wherein said mercuric salt is selected from the group consisting of mercuric sulphate and mercuric chlorate.

8. A method according to claim 6, wherein said reaction is performed with a stoichiometric excess of the mercuric salt.

9. A method according to claim 6, wherein said reaction is performed in the presence of a water-miscible organic salt.

10. A method according to claim 9, wherein said solvent is tetrahydrofuran.

* * * * *